United States Patent
Kakutani et al.

(10) Patent No.: US 8,933,415 B2
(45) Date of Patent: Jan. 13, 2015

(54) LASER ION SOURCE AND HEAVY PARTICLE BEAM THERAPY EQUIPMENT

(71) Applicant: Kabushiki Kaisha Toshiba, Minato-ku (JP)

(72) Inventors: Akiko Kakutani, Kanagawa (JP); Takayuki Sako, Kanagawa (JP); Kiyokazu Sato, Tokyo (JP); Yoshiharu Kanai, Kanagawa (JP); Takeshi Yoshiyuki, Kanagawa (JP); Tsutomu Kurusu, Tokyo (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 14/175,054

(22) Filed: Feb. 7, 2014

(65) Prior Publication Data
US 2014/0235918 A1  Aug. 21, 2014

(30) Foreign Application Priority Data
Feb. 21, 2013  (JP) ................. 2013-032301

(51) Int. Cl.
*G21K 5/04* (2006.01)
*H01J 27/24* (2006.01)
*A61N 5/10* (2006.01)

(52) U.S. Cl.
CPC ............... *H01J 27/24* (2013.01); *A61N 5/1077* (2013.01); *A61N 2005/1088* (2013.01)

USPC ............... 250/423 P; 250/424; 315/111.01; 315/111.81

(58) Field of Classification Search
CPC ......... H01J 37/04; H01J 37/08; H01J 27/022; H01J 27/24; H01J 27/26; H01J 27/02
USPC ............ 315/111.01, 111.81; 250/423 R, 424, 250/425, 423 P
See application file for complete search history.

(56) References Cited

U.S. PATENT DOCUMENTS

2013/0207000 A1* 8/2013 Gunther et al. ........... 250/396 R

FOREIGN PATENT DOCUMENTS

| JP | 3713524 | 11/2005 |
|---|---|---|
| JP | 2009-37764 | 2/2009 |
| JP | 2009-217938 | 9/2009 |
| JP | 2012-99273 | 5/2012 |

* cited by examiner

Primary Examiner — Nicole Ippolito
(74) Attorney, Agent, or Firm — Oblon, Spivak, McClelland, Maier & Neustadt, L.L.P.

(57) ABSTRACT

One embodiment of a particle accelerator includes: a vacuum container with its inside evacuated to produce vacuum, the vacuum container being formed with a laser beam entrance window for allowing a laser beam to enter; a target arranged in the vacuum container so as to be irradiated with a laser beam to generate ions; and a condenser lens for focusing the laser beam onto the target. The condenser lens is arranged at the laser beam entrance window of the vacuum container, and takes a role of a vacuum bulkhead.

10 Claims, 6 Drawing Sheets

LASER ION SOURCE AND HEAVY PARTICLE BEAM THERAPY EQUIPMENT

CROSS REFERENCE TO RELATED APPLICATION

This application is based upon and claims the benefit of priority from Japanese Patent Application No. 2013-32301, filed on Feb. 21, 2013, the entire content of which is incorporated herein by reference.

FIELD

Embodiments described herein relates to a laser ion source that generates ions when irradiated with a laser beam and also to heavy particle therapy equipment using such the laser ion source.

BACKGROUND

Techniques of causing electric discharge to occur in gas to produce ions are widely known as ion generating techniques. Microwaves and electron beams are employed to make electric discharge occur.

On the other hand, the laser ion source employing a laser by definition is designed to irradiate a target with a condensed laser beam to evaporate the element of the target and ionize it to generate plasma. The laser ion source is a device for transporting the ions intact as they are contained in the plasma and producing an ion beam by accelerating the ions at the time of extracting the ions (see, for example, Japanese Patent Publication No. 3,713,524 and Japanese Patent Application Laid-Open Publication No. 2009-37764, the entire content of which is incorporated herein by reference). Thus, the laser ion source can generate ions by irradiating a solid target with a laser beam and hence is advantageous when generating a pulsed high current for multivalent ions.

The ions generated by the laser ion source have an initial velocity in a direction perpendicular to the surface of the solid target. Therefore, the laser ion source can be made to transport ions by extending the transport pipe showing an electric potential same as the ion generating section downstream as viewed in the transporting direction. Furthermore, the laser ion source can be so arranged as to block unnecessary ions from passing by setting up electrodes on the plasma transport route and applying a positive electric field to the plasma on the plasma transport route (see Japanese Patent Application Laid-Open Publication No. 2012-99273 the entire content of which is incorporated herein by reference).

Meanwhile, Review of Scientific Instruments 81, 02A510 (published in 2010) (to be referred to as Literature 1 hereinafter), the entire content of which is incorporated herein by reference, describes a technique for the laser beam injection system of the laser ion source. With the technique, the laser beam emitted from a YAG laser is led to a vacuum container from the outside of the vacuum container by way of two mirrors. The laser beam is introduced into the vacuum container through a vacuum window of the vacuum container. In the vacuum container, the laser beam is reflected by a mirror and made to enter a lens. The laser beam is then condensed by the lens and irradiated onto a target.

The laser beam injection system described in Literature 1 requires axial alignment of the mirror and the lens in the vacuum container. Since the mirror and the lens of the optical system are arranged in the vacuum container, the use of a drive mechanism such as a motor is necessary to adjust the relative axial positions of the mirror and the lens from the outside of the vacuum container. Therefore, the laser ion source of the above-cited Literature 1 is accompanied by a problem of a complex structure involving wirings drawn outside the vacuum container.

With the laser ion source as described in the above-cited Literature 1, when a mirror and a lens are arranged in the plasma generation section thereof, they can be stained by laser ablation particles adhering to them to consequently degrade the target irradiation performance of the laser beam. Then, the mirror and the lens may need to be replaced and a stain prevention mechanism (of arranging a transparent film reel and a take-up reel in the vacuum container, for example) may have to be provided.

Therefore, with such a laser ion source, the axial position of the optical system needs to be adjusted again after replacing the mirror and the lens. Additionally, a problem of a complex structure arises when a stain prevention mechanism is arranged in the vacuum container.

Thus, the problem to be solved by the present invention is to provide a laser ion source in which the condenser lens can be axially aligned with ease and which has a simplified structure and also to provide heavy particle beam therapy equipment employing such a laser ion source.

BRIEF DESCRIPTION OF THE DRAWINGS

The features and advantages of the present invention will become apparent from the discussion hereinbelow of specific, illustrative embodiments thereof presented in conjunction with the accompanying drawings, in which.

DETAILED DESCRIPTION

According to one embodiment, there is provided a laser ion source comprising: a vacuum container with its inside evacuated to produce vacuum, the vacuum container being formed with a laser beam entrance window for allowing a laser beam to enter; a target arranged in the vacuum container so as to be irradiated with a laser beam to generate ions; and a condenser lens for focusing the laser beam onto the target; the condenser lens being arranged at the laser beam entrance window of the vacuum container; the condenser lens taking a role of vacuum bulkhead.

Further, according to another embodiment, there is provided a laser ion source comprising: a vacuum container with its inside evacuated to produce vacuum, the vacuum container being formed with a laser beam entrance window for allowing a laser beam to enter; a target arranged in the vacuum container so as to be irradiated with a laser beam to generate ions; a vacuum window arranged at the laser beam entrance window of the vacuum container to introduce a laser beam into the vacuum container and having a function of a vacuum bulkhead; and a condenser lens arranged outside the vacuum container to focus the laser beam onto the target through the vacuum window.

The heave particle beam therapy equipment of an embodiment comprises one of the above-described embodiments of laser ion source.

Now, embodiments of laser ion sources according to the present invention and also embodiments of heavy particle beam therapy equipment comprising any of the embodiments of laser ion source will be described below by referring to the accompanying drawings.

(Heavy Particle Therapy Equipment)

Figure 1:
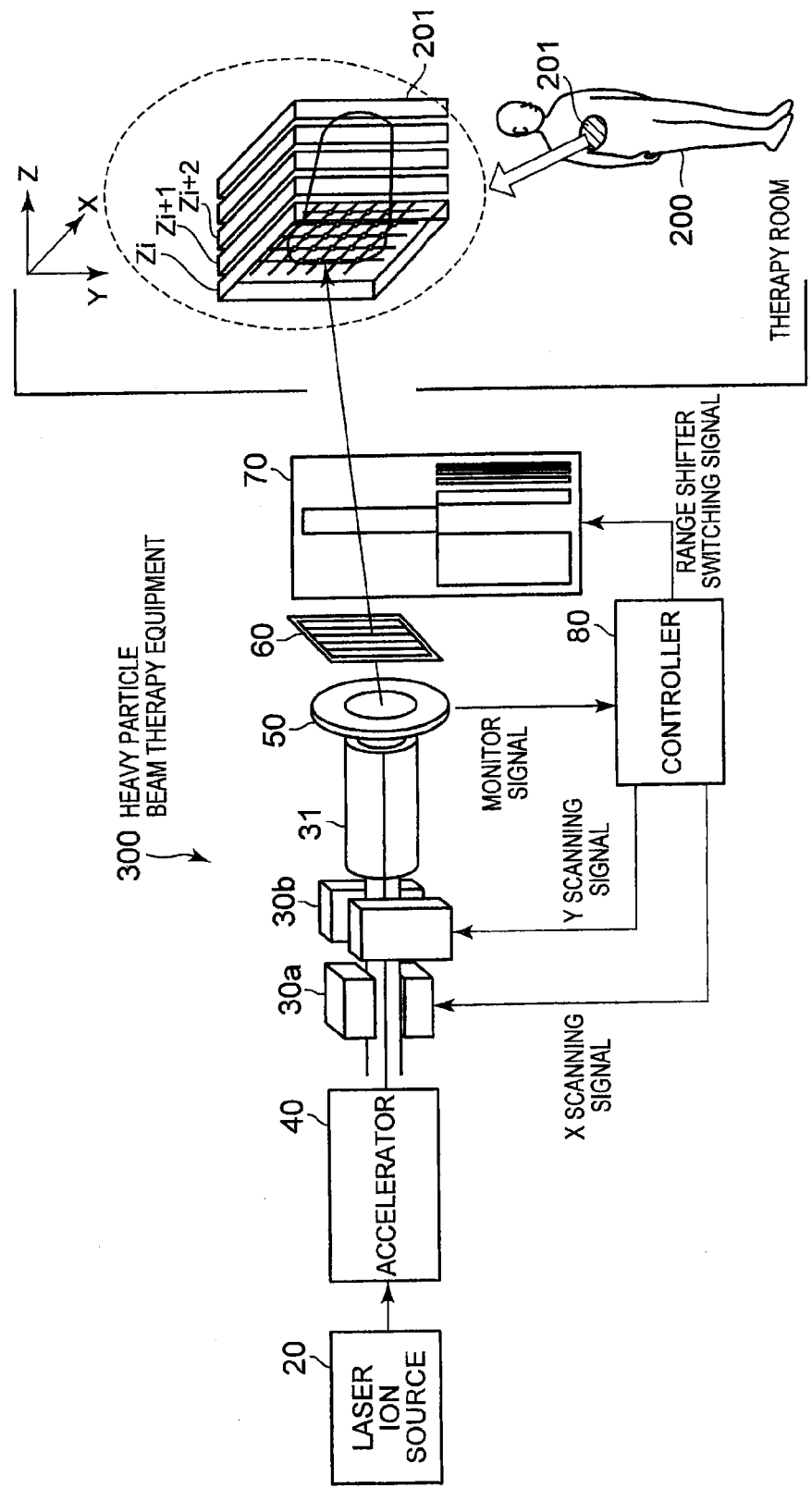
FIG. 1 is a schematic illustration of heavy particle beam therapy equipment comprising an embodiment of laser ion source according to the present invention, showing an exemplar configuration thereof.

FIG. 1 is a schematic illustration of heavy particle beam therapy equipment comprising an embodiment of laser ion source according to the present invention, showing an exemplar configuration thereof.

As shown in FIG. 1, a heavy particle therapy equipment 300 has a laser ion source 20, an accelerator 40, which may be a linear accelerator 8, an electromagnet 30a for X-axis scanning, an electromagnet 30b for Y-axis scanning, a vacuum duct 31, a dose monitor section 50, a ridge filter 60, a range shifter 70, a controller 80 and so on.

The heavy particle beam therapy equipment 300 generates heavy particle ions by means of the laser ion source 20, then produces a particle beam by accelerating the generated heavy particle ions by means of the accelerator 40 and irradiates the particle beam to the diseased part (tumor cells) 201 of a patient 200 for treatment. The heavy particle beam therapy equipment 300 can discretize the diseased part 201 into three-dimensional lattice points and execute a three-dimensional scanning irradiation process of sequentially scanning the lattice points with a fine diameter particle beam.

More specifically, with the heavy particle beam therapy equipment 300, the diseased part 201 is divided internal flat unit pieces that are referred to as slices and the two-dimensional lattice points of each of the slices including slices $Z_i$, $Z_{i+1}, Z_{i+2}, \ldots$ (the lattice points in the X-axis direction and the Y-axis direction in the coordinate system shown at the upper right corner of FIG. 1) are sequentially scanned for three-dimensional scanning.

The heavy particle ions generated by the laser ion source 20 are accelerated by the linear accelerator 8 or some other accelerator 40 that may be a synchrotron to raise the energy level of the heavy particle ions and produce a particle beam that can penetrate deep into the diseased part 201.

The electromagnet 30a for X-axis scanning and the electromagnet 30b for Y-axis scanning deflect the particle beam respectively in the X-direction and in the Y-direction so as to make it two-dimensionally scan the surface of each of the slices. The range shifter 70 controls the position of the diseased part 201 in the Z-axis direction. The range shifter 70 is formed, for example, by using a plurality of thick acrylic plates. The energy of the particle beam that passes the range shifter 70 and hence the intra-body trajectory of the particle beam can be made to vary stepwise according to the position of each of the slices of the diseased part 201 in the Z-axis direction. The intra-body trajectory is normally made to vary at regular intervals by means of the range shifter 70 and the intervals correspond to the gaps separating the corresponding lattice points in the Z-axis direction. Techniques that can be employed to make the intra-body trajectory vary include a technique of altering the energy itself of the particle beam by controlling an upstream device in addition to the technique of inserting an energy attenuating device such as a range shifter 70 in the route of the particle beam.

The ridge filter 60 is provided to spread the sharp peak, which is referred to as black peak, of the dose in the depth direction of the patient body. The width of the black peak spread by the ridge filer 60 is made to be equal to the thickness of each of the slices and hence the intervals of the corresponding lattice points in the Z-axis direction. The ridge filter 60 for three-dimensional scanning irradiation is formed by arranging a plurality of rod-shaped aluminum members showing a substantially isosceles triangle cross section. The black peak can be spread by utilizing the difference in the route length that arises when the particle beam passes the isosceles triangles. A desired spread width can be obtained by selecting appropriate profiles for the isosceles triangles.

The dose monitor section 50 is for monitoring the dose of irradiation. It is formed by arranging in its casing an ionization chamber that collects the electric charges produced by the ionization effect of the particle beam by means of parallel electrodes, a SEM (secondary electron monitor) for gauging the secondary electrons emitted from the secondary electron emission membrane arranged in the casing and other members.

(First Embodiment of Laser Ion Source)

Figure 2:
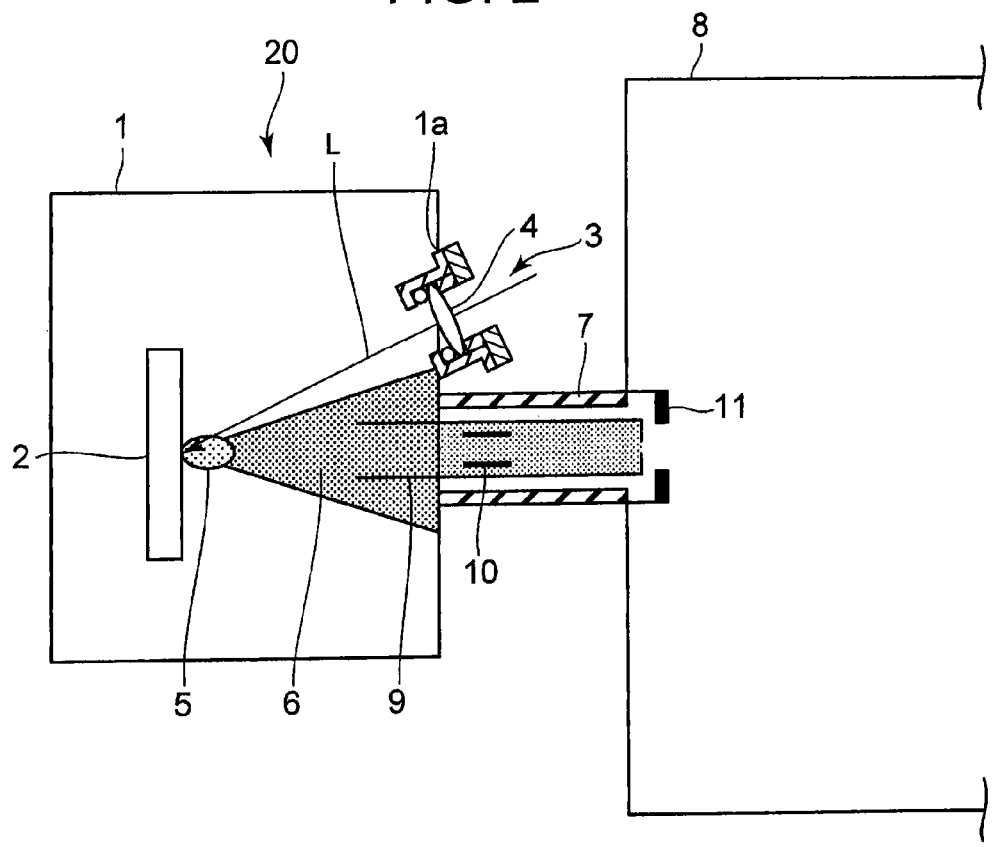
FIG. 2 is a schematic cross-sectional view of the first embodiment of a laser ion source according to the present invention, showing the configuration thereof.
Figure 3:
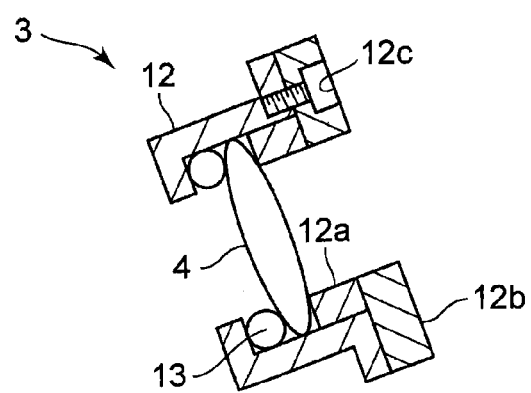
FIG. 3 is an enlarged schematic cross-sectional view of the lens fitting mechanism of FIG. 2.

FIG. 2 is a schematic cross-sectional view of the first embodiment of a laser ion source according to the present invention, showing the configuration thereof. FIG. 3 is an enlarged schematic cross-sectional view of the lens fitting mechanism of FIG. 2.

As shown in FIG. 2, a vacuum container 1 is made of a material, such as stainless steel, that is highly corrosion-resistant and chemical-resistant and hardly emits gas. A target 2, which may be a mass of an element that turns ions or a material containing such an element, is arranged in the inside of the vacuum container 1. The target 2 typically is a carbon-based plate-shaped member.

A high voltage is applied to the vacuum container 1 from a high voltage power source (not shown). A positive electric potential is applied when a positive ion beam is to be produced, whereas a negative electric potential is applied when a negative ion beam is to be produced. A positive electric potential is applied in this embodiment. The vacuum container 1 is formed with an exhaust port (not shown) and a vacuum pump (not shown) is connected to the exhaust port to evacuate the vacuum container 1 and create a vacuum in the inside of the vacuum container 1.

A laser beam entrance window 1a is formed on the vacuum container 1 as part of the wall surfaces thereof, more specifically at an upper part of a lateral wall surface, to allow a laser beam to enter the vacuum container 1. A lens fitting mechanism 3 is rigidly secured to the laser beam entrance window 1a. A condenser lens 4 that operates as an optical system for condensing a laser beam L is fitted to the lens fitting mechanism 3. The laser beam L that is emitted from a laser beam source (not shown) enters the vacuum container 1 through the condenser lens 4 and subsequently the condensed laser beam L is irradiated onto the target 2. For example, a $CO_2$ laser or an Nd-YAG laser can be used for the laser beam source.

A transport pipe 9 for taking out ions is arranged at a lateral surface (at the right lateral surface in FIG. 2) of the vacuum container 1. Electrodes 10 are arranged in the transport pipe 9 to eliminate unnecessary ions by applying a positive electric field. The transport pipe 9 is held to a positive electric potential and is arranged in an insulating tube 7, the inside of which is held to a vacuum condition. The insulating tube 7 is connected at one of the opposite ends thereof to a lateral surface of the vacuum container 1 and the other end is connected to a linear accelerator (RFQ: radio frequency quadrupole) 8 that is held to the ground potential. Electrodes 11 are held to the ground potential and arranged near an end of the transport pipe 9 in the linear accelerator 8. The electrodes 11 operate for intensifying the ion drawing out electric field.

The lens fitting mechanism 3 is rigidly secured to the vacuum container 1 by welding a lens holder 12 (see FIG. 2) to the vacuum container 1. The lend holder 12 has a shape of a cylinder. The condenser lens 4 is mounted in the lens holder 12 as shown in FIG. 2. The condenser lens 4 is mechanically positioned in place and supported by the lens holder 12. The lens holder 12 forces the condenser lens 4 to contact an O-ring 13 under pressure and the O-ring 13 and the condenser lens 4 are sealed to make the condenser lens 4 take a role of vacuum bulkhead in the inside of the vacuum container 1.

The mechanism for forcing the condenser lens 4 to contact the O-ring 13 under pressure includes a ring ferrule 12a that is brought into contact with the condenser lens 4, a securement ring 12b for pressing and rigidly holding the condenser lens 4 in position by way of the ring ferrule 12a and screw bolts 12c for securing the securement ring 12b to the lens holder 12. The lens holder 12, the O-ring 13, the ring ferrule 12a and the securement ring 12b are arranged coaxially. The ring ferrule 12a is made of a material that does not damage the condenser lens 4 such as polytetrafluoroethylene (PTFE). In this way, the condenser lens 4 is made to be integral with the vacuum container 1 and operate as vacuum bulkhead.

Now, the operation and the advantages of this embodiment will be described below.

Assume here that the inside of the vacuum container 1 is satisfactorily evacuated to establish a vacuum condition there by means of the vacuum pump connected to the exhaust port (not shown). Also assume, for example, a positive electric potential is applied to the vacuum container 1 and a positive electric potential higher than the electric potential of the vacuum container 1 is applied to the transport pipe 9, while a positive electric field is applied to the electrodes 10 and the ground potential is applied to the electrodes 11.

In this condition, laser beam L coming from the laser beam source (not shown), which is pulse-driven, is condensed by the condenser lens 4 that is made to be integral with the vacuum container 1 and irradiated onto the target 2. A minute portion of the target 2 is heated by the laser beam L to high temperatures at the focal point on the target 2 where the laser beam L is focused. The portion that is heated to high temperatures turns into plasma, which is referred to as laser ablation plasma 5.

The laser application plasma 5 is transported through the transport pipe 9 at a high positive electric potential and only necessary ions 6 are accelerated by the potential difference between the transport pipe 9 and the linear accelerator 8 at the ground potential to become an ion beam, which is then made to enter the linear accelerator 8. The unnecessary ions are eliminated by the electrodes 10. Then, the ion beam is further accelerated by the linear accelerator 8.

Meanwhile, the condenser lens 4 for condensing the laser beam L may be arranged either inside or outside the vacuum container 1 depending on the focal length of the condenser lens 4 and the shape of the vacuum container 1. However, since a condenser lens 4 having a shorter focal length can more raise the laser energy density on the target 2 than a condenser lens having a longer focal length, the condenser lens 4 is generally arranged in the inside of the vacuum container 1 when generating ions of a higher valence number. In such an instance, then, the condenser lens 1 is generally arranged on the optical axis of the laser in the vacuum container 1, using the vacuum window through which the laser beam L passes as vacuum bulkhead.

It is not necessary to arrange the mirror and the condenser lens 4 in the plasma generation section in the vacuum container 1 in this embodiment. Therefore, it is no longer necessary to replace the mirror and the lens and provide a stain prevention mechanism, so that the structure of the entire laser ion source can be simplified.

Additionally, since the condenser lens 4 is employed as vacuum bulkhead to make the use of a vacuum window unnecessary in this embodiment, the number of components of this embodiment can be reduced and the energy loss of the laser beam L can also be reduced.

Furthermore, the condenser lens 4 is employed as a vacuum bulkhead, so that the components of a vacuum window are no longer necessary in this embodiment. Additionally, since the condenser lens 4 is made to be integral with the vacuum container 1, the condenser lens 4 can be made free from any axial alignment operation.

As described above, the condenser lens 4 of this embodiment can be axially aligned with ease and the structure of the embodiment can be simplified.

(Second Embodiment of Laser Ion Source)

Figure 4:
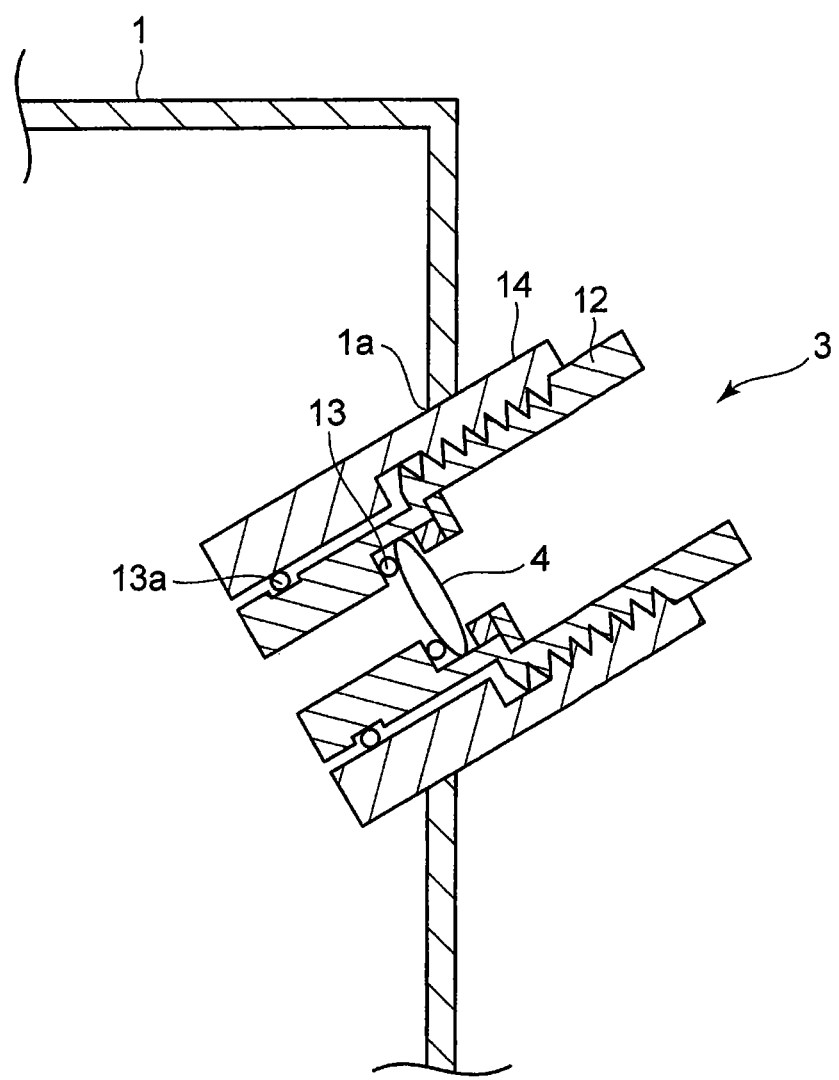
FIG. 4 is an enlarged schematic cross-sectional view of the lens fitting mechanism of the second embodiment of laser ion source according to the present invention.

FIG. 4 is an enlarged schematic cross-sectional view of the lens fitting mechanism of the second embodiment of a laser ion source according to the present invention. In the following embodiments of laser ion source, the components same as or similar to those of the first embodiment are denoted respectively by the same reference symbols and will not be described repeatedly.

As shown in FIG. 4, this embodiment differs from the first embodiment in that the condenser lens 4 is made movable in the direction of the laser optical axis in this embodiment unlike the first embodiment. More specifically, the inner peripheral surface of holder fitting member 14 is threaded to produce a female screw there and the outer peripheral surface of the lens holder 12 is threaded to produce a male screw that can be driven into the female screw. The holder fitting member 14 is formed to show a cylindrical profile and rigidly secured to the vacuum container 1 by welding.

With this arrangement, the condenser lens 4 can be driven to move in the direction of the optical axis of the laser to adjust the focus position thereof by rotating the lens holder 12.

The vacuum sealing structure of the lens holder 12 of this embodiment is similar to that of the first embodiment. Additionally, the connecting area of the lens holder 12 and the holder fitting member 14 can be vacuum sealed, for example, by means of an O-ring 13a rigidly secured to the lens holder 12.

Thus, this embodiment does not require any axial alignment of the condenser lens 4 and the condenser lens 4 can be moved in the direction of the optical axis to adjust the focus position thereof without damaging the vacuum condition, as the condenser lens 4 is made to take a role of a vacuum bulkhead.

(Third Embodiment of Laser Ion Source)

Figure 5:
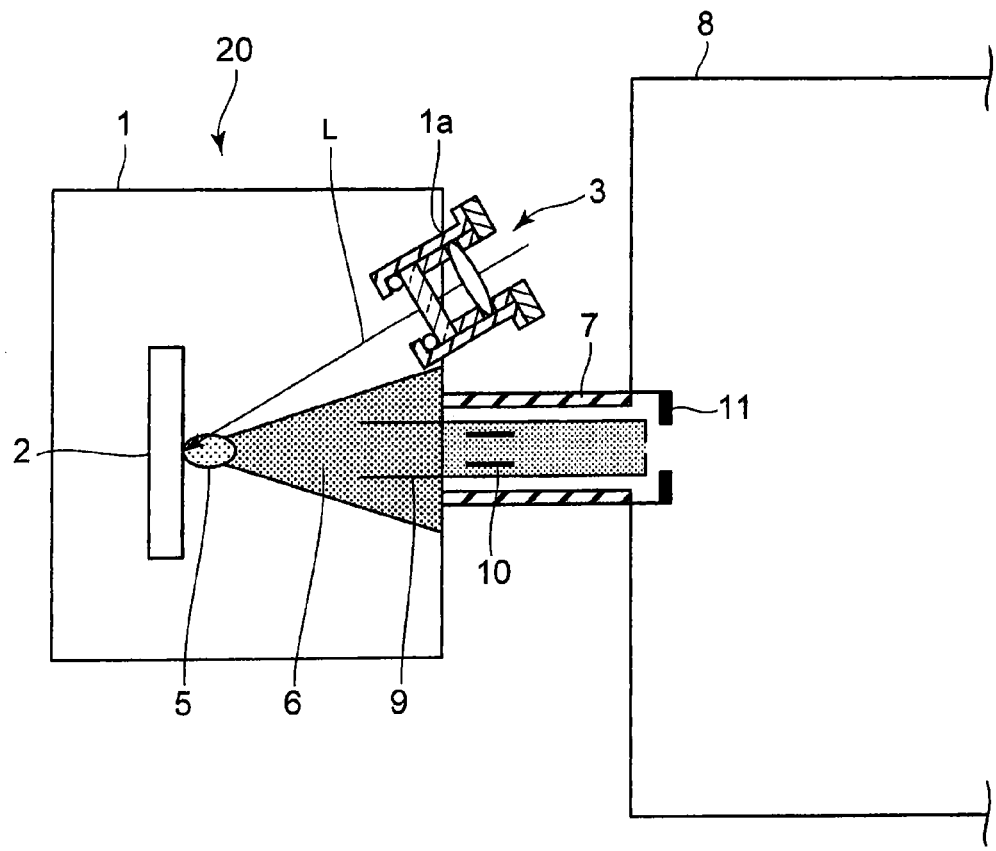
FIG. 5 is a schematic cross-sectional view of the third embodiment of a laser ion source according to the present invention, showing the configuration thereof.
Figure 6:
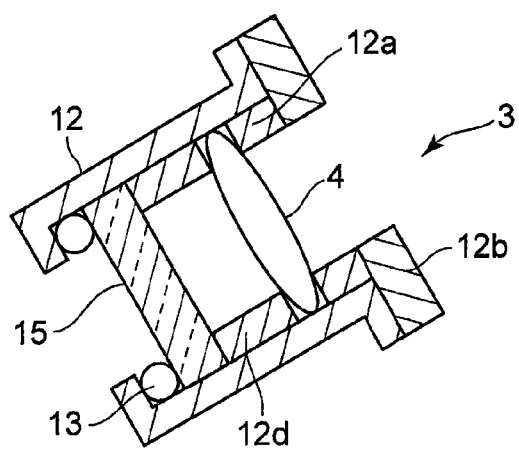
FIG. 6 is an enlarged schematic cross-sectional view of the lens fitting mechanism of FIG. 5.

FIG. 5 is a schematic cross-sectional view of the third embodiment of a laser ion source according to the present invention, showing the configuration thereof. FIG. 6 is an enlarged schematic cross-sectional view of the lens fitting mechanism of FIG. 5.

As shown in FIGS. 5 and 6, this embodiment differs from the first embodiment in that the vacuum bulkhead of lens holder 12 is sealed by means of a vacuum window 15 and an O-ring, and the condenser lens 4 is arranged outside the vacuum bulkhead in this embodiment.

The vacuum window 15 is made of a material that transmits laser beam L such as glass. Preferably, the surface of the vacuum window 15 is provided with an anti-reflection coat so as to efficiently transmit laser beam L. A ring ferrule 12d typically made of polytetrafluoroethylene (PTFE) is arranged outside the vacuum bulkhead of the vacuum window 15 so as not to damage the vacuum window 15 and the condenser lens 4. The condenser lens 4 is pressed against the ring ferrule 12d by means of another ring ferrule 12a and rigidly secured in position as the securement ring 12 is rigidly secured by means of a screw.

Thus, as the vacuum window 15 is employed as vacuum bulkhead in this embodiment, the condenser lens 4 is prevented from being stained by ablation particles.

Additionally, as the condenser lens 4 and the vacuum window 15 are integrally arranged in the vacuum container 1, it is no longer necessary to axially align the condenser lens 4.

Note that the position of the condenser lens 4 of this embodiment in the direction of the optical axis thereof can be adjusted by altering the thickness of the ring ferrule 12a and that of the ring ferrule 2d.

(Fourth Embodiment of Laser Ion Source)

Figure 7:
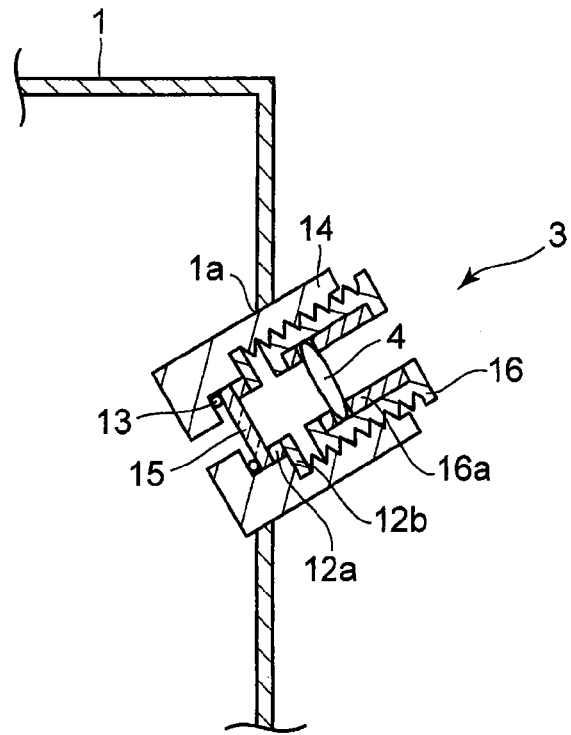
FIG. 7 is an enlarged schematic cross-sectional view of the vacuum window and the lens fitting mechanism of the fourth embodiment of a laser ion source according to the present invention.

FIG. 7 is an enlarged schematic cross-sectional view of the vacuum window and the lens fitting mechanism of the fourth embodiment of laser ion source according to the present invention.

As shown in FIG. 7, this embodiment differs from the third embodiment in that the condenser lens 4 in the lens holder 12 is made to be movable in the direction of the optical axis of the laser in the embodiment unlike the third embodiment. More specifically, a vacuum window 15 is arranged at the vacuum side of the holder fitting member 14. The vacuum window 15 is fitted to the side of the O-ring 13 relative to the ring ferrule 12a and rigidly secured in position as the securement ring 12b is rigidly secured by means of a screw.

Movable lens holder 16 is made to show a cylindrical profile and arranged to be coaxial with the holder fitting member 14. In this embodiment, the inner peripheral surface of holder fitting member 14 is threaded to produce a female screw there and the outer peripheral surface of the movable lens holder 16 is threaded to produce a male screw that can be driven into the female screw. With this arrangement, the condenser lens 4 can be driven to move in the direction of the optical axis of the laser to consequently adjust the focus position thereof by rotating the movable lens holder 16.

The condenser lens 4 is rigidly secured to the movable lens holder 16 by means of a ring ferrule 16a. Although not shown in FIG. 7, the ring ferrule 16a can be rigidly secured by means of a screw bolts just like the vacuum window 15. The position of the condenser lens 4 can be adjusted in the direction of the optical axis of the laser by altering the axial length of the ring ferrule 16a.

Thus, with this embodiment, it is no longer necessary to axially align the condenser lens 4 and the position of the condenser lens 4 can be adjusted in the direction of the optical axis outside the vacuum and hence without damaging the vacuum condition.

(Fifth Embodiment of Laser Ion Source)

Figure 8:
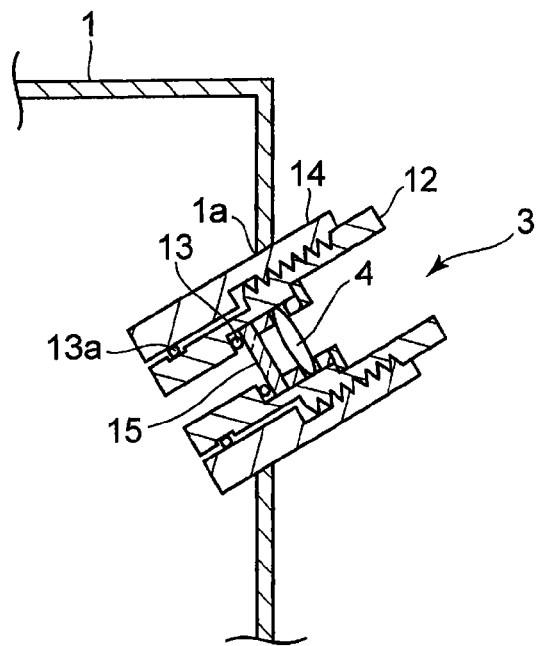
FIG. 8 is an enlarged schematic cross-sectional view of the vacuum window and the lens fitting mechanism of the fifth embodiment of laser ion source according to the present invention.

FIG. 8 is an enlarged schematic cross-sectional view of the vacuum window and the lens fitting mechanism of the fifth embodiment of laser ion source according to the present invention.

As shown in FIG. 8, this embodiment differs from the third embodiment in that the condenser lens 4 and the vacuum window 15 in the lens holder 12 are made movable in the direction of the optical axis of the laser in this embodiment unlike the third embodiment. More specifically, the vacuum window 15 and the condenser lens 4 are arranged integrally in the lens holder 12.

Additionally, in this embodiment, the inner peripheral surface of holder fitting member 14 is threaded to produce a female screw there and the outer peripheral surface of the lens holder 12 is threaded to produce a male screw that can be driven into the female screw. With this embodiment, the position of the condenser lens 4 and that of the vacuum window 15 can be adjusted in the direction of the optical axis of the laser by rotating the lens holder 12. Then, as a result, it is possible to adjust the focal position of the condenser lens 4.

Furthermore, in this embodiment, the vacuum window 15 is sealed by an O-ring 13 and the interface of the holder fitting member 14 and the lens holder 12 is sealed by another O-ring 13a.

Thus, with this embodiment, it is no longer necessary to axially align the condenser lens 4 and the position of the condenser lens 4 can be adjusted in the direction of the optical axis without damaging the vacuum condition.

(Sixth Embodiment of Laser Ion Source)

Figure 9:
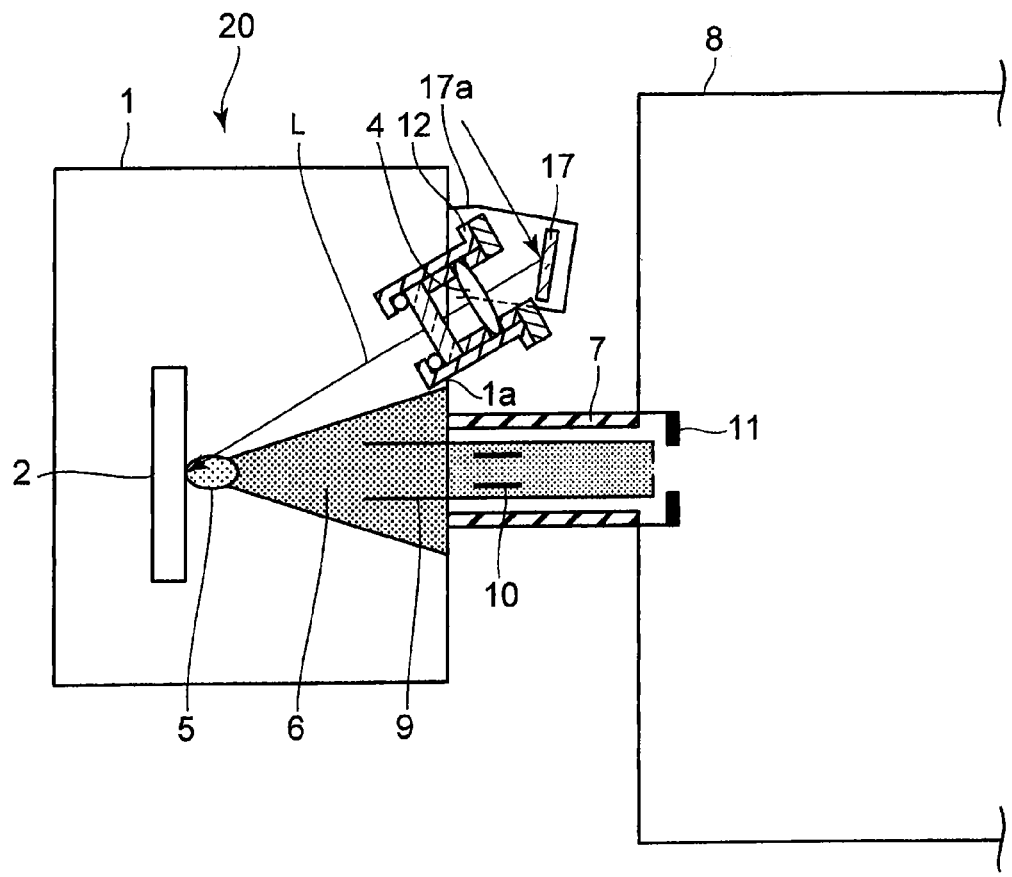
FIG. 9 is a schematic cross-sectional view of the sixth embodiment of a laser ion source according to the present invention, showing the configuration thereof.
Figure 10:
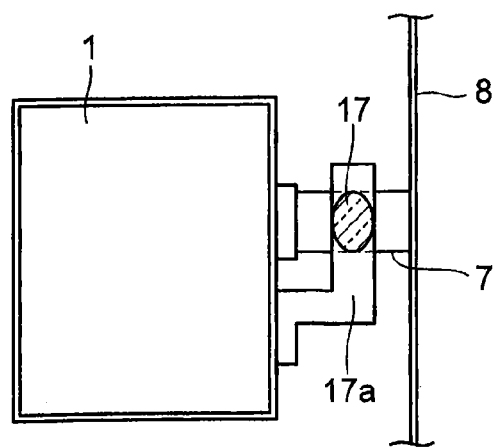
FIG. 10 is a schematic plan view of the lens fitting mechanism of FIG. 9.

FIG. 9 is a schematic cross-sectional view of the sixth embodiment of laser ion source according to the present invention, showing the configuration thereof. FIG. 10 is a schematic plan view of the lens fitting mechanism of FIG. 9.

As shown in FIGS. 9 and 10, this embodiment differs from the third embodiment in that a mirror holder 17a is rigidly secured to the outer lateral surface of the vacuum container 1 and a mirror 17 is rigidly secured to the mirror holder 17a in this embodiment unlike the third embodiment. The mirror 17 is for causing the laser beam L to enter the condenser lens 4.

The mirror holder 17a is made of a member that does not vibrate and is reproducible such as a metal thin plate. A mechanical position adjusting mechanism is arranged at the mirror holder 17a. The mirror 17 is axially aligned with the condenser lens 4 along the optical axis of the laser beam L.

Thus, in this embodiment, the mirror 17 is made to be integral with the vacuum container 1 by means of the mirror holder 17a to make the position of arrangement of the mirror 17 freely selectable and eliminate the necessity of axial alignment of the condenser lens 4.

(Other Embodiments)

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, while the lens holder 12 is rigidly secured to the laser beam entrance window 1a of the vacuum container 1 and the condenser lens 4 is fitted to the lens holder 12 in the first embodiment of laser ion source, the present invention is by no means limited to such an arrangement and the condenser lens 4 may alternatively be fitted directly to the laser beam entrance window 1*a* of the vacuum container 1.

The above-described arrangement of the sixth embodiment may be combined with any of the second through fifth embodiments.

What is claimed is:

1. A laser ion source comprising:
    a vacuum container with its inside evacuated to produce vacuum, the vacuum container being formed with a laser beam entrance window for allowing a laser beam to enter;
    a target arranged in the vacuum container so as to be irradiated with the laser beam to generate ions; and
    a condenser lens for focusing the laser beam onto the target, the condenser lens being arranged at the laser beam entrance window of the vacuum container, the condenser lens taking a role of a vacuum bulkhead.

2. The laser ion source according to claim 1, wherein the condenser lens is made movable in a direction of optical axis of the laser beam.

3. The laser ion source according to claim 1, wherein a mirror holder is rigidly secured to an outer surface of the vacuum container and a mirror is fitted to the mirror holder to introduce the laser beam into the vacuum container.

4. A heavy particle beam therapy equipment comprising a laser ion source according to claim 1.

5. A laser ion source, comprising:
    a vacuum container with its inside evacuated to produce vacuum, the vacuum container being formed with a laser beam entrance window for allowing a laser beam to enter:
    a target arranged in the vacuum container so as to be irradiated with a laser beam to generate ions;
    a vacuum window arranged at the laser beam entrance window of the vacuum container to introduce a laser beam into the vacuum container and having a function of a vacuum bulkhead; and
    a condenser lens arranged outside the vacuum container to focus the laser beam onto the target through the vacuum window, wherein
    the vacuum window and the condenser lens are arranged in a direction of optical axis of the laser beam and made integrally movable also in the direction of the optical axis of the laser beam.

6. The laser ion source according to claim 5, wherein the condenser lens is made movable in the direction of optical axis of the laser beam.

7. A heavy particle beam therapy equipment comprising a laser ion source according to claim 5.

8. A laser ion source, comprising:
    a vacuum container with its inside evacuated to produce vacuum, the vacuum container being formed with a laser beam entrance window for allowing a laser beam to enter;
    a target arranged in the vacuum container so as to be irradiated with a laser beam to generate ions;
    a vacuum window arranged at the laser beam entrance window of the vacuum container to introduce a laser beam into the vacuum container and having a function of a vacuum bulkhead; and
    a condenser lens arranged outside the vacuum container to focus the laser beam onto the target through the vacuum window, wherein
    a mirror holder is rigidly secured to an outer surface of the vacuum container and a minor is fitted to the mirror holder to introduce the laser beam into the vacuum container.

9. The laser ion source according to claim 8, wherein the condenser lens is made movable in a direction of optical axis of the laser beam.

10. A heavy particle beam therapy equipment comprising a laser ion source according to claim 8.

* * * * *